US009700215B2

(12) United States Patent
Levine

(10) Patent No.: US 9,700,215 B2
(45) Date of Patent: Jul. 11, 2017

(54) SYSTEMS AND METHODS FOR ASSESSING VASCULATURE HEALTH AND BLOOD CLOTS

(71) Applicant: Marc-Alan Levine, Pottstown, PA (US)

(72) Inventor: Marc-Alan Levine, Pottstown, PA (US)

(73) Assignee: Makaha Medical, LLC., Pottstown, PA (US)

( * ) Notice: Subject to any disclaimer, the term of this patent is extended or adjusted under 35 U.S.C. 154(b) by 518 days.

(21) Appl. No.: 14/052,721

(22) Filed: Oct. 12, 2013

(65) Prior Publication Data

US 2014/0114144 A1   Apr. 24, 2014

Related U.S. Application Data

(60) Provisional application No. 61/718,107, filed on Oct. 24, 2012.

(51) Int. Cl.
*A61B 5/02* (2006.01)
*A61B 5/145* (2006.01)
(Continued)

(52) U.S. Cl.
CPC ...... *A61B 5/02007* (2013.01); *A61B 5/14503* (2013.01); *A61B 5/14539* (2013.01);
(Continued)

(58) Field of Classification Search
CPC ......... A61B 5/02; A61B 5/145; A61B 8/0833; A61B 8/085; A61B 8/0891; A61B 8/08;
(Continued)

(56) References Cited

U.S. PATENT DOCUMENTS 4,319,580 A   3/1982 Colley et al.
4,354,502 A   10/1982 Colley et al.
(Continued)

FOREIGN PATENT DOCUMENTS

WO   WO 2013/181137   12/2013

OTHER PUBLICATIONS

Khatri, Rakesh, et al. "Blood—brain barrier, reperfusion injury, and hemorrhagic transformation in acute ischemic stroke." Neurology 79.13 Supplement 1 (2012): S52-S57.*
(Continued)

*Primary Examiner* — William Thomson
*Assistant Examiner* — Nathan A Baldwin

(57) ABSTRACT

A system and method for determining a pH level of blood in a vessel of a patient including a flexible elongated member configured and dimensioned for insertion in the vessel of the patient, a sensor positioned at the distal portion of the elongated member, and a connector connecting the elongated member to an indicator. The sensor measures the pH level of blood downstream of the blood clot. A system and method are also provided for determining a density of a blood clot in a vessel of a patient for subsequent selection of a treatment method. The system includes a sensor positioned at the distal portion of the elongated member, and a connector connecting the elongated member to an indicator, wherein the sensor determines the density of the blood clot and the indicator provides an indication of the density of the clot.

11 Claims, 20 Drawing Sheets

(51) Int. Cl.
*A61B 8/08* (2006.01)
*A61B 8/12* (2006.01)
*A61B 8/00* (2006.01)
*A61B 5/00* (2006.01)

(52) U.S. Cl.
CPC .......... *A61B 5/14542* (2013.01); *A61B 8/085* (2013.01); *A61B 8/0891* (2013.01); *A61B 8/12* (2013.01); *A61B 8/485* (2013.01); *A61B 5/6852* (2013.01); *A61B 8/445* (2013.01)

(58) Field of Classification Search
CPC ....... A61B 8/12; A61B 5/6851; A61B 5/6852; A61B 8/445
See application file for complete search history.

(56) References Cited

U.S. PATENT DOCUMENTS

| | | | |
|---|---|---|---|
| 5,054,882 A | 10/1991 | Riccitelli et al. | |
| 5,125,410 A | 6/1992 | Misono et al. | |
| 5,271,398 A | 12/1993 | Schlain et al. | |
| 5,307,816 A | 5/1994 | Hashimoto et al. | |
| 5,348,015 A | 9/1994 | Moehring et al. | |
| 5,441,051 A | 8/1995 | Hileman et al. | |
| 5,477,860 A | 12/1995 | Essen-Moller | |
| 5,522,389 A | 6/1996 | Fischer et al. | |
| 5,743,259 A | 4/1998 | Kruse et al. | |
| 5,848,965 A | 12/1998 | Essen-Moller | |
| 5,928,155 A | 7/1999 | Eggers et al. | |
| 6,125,290 A | 9/2000 | Miesel | |
| 6,125,291 A | 9/2000 | Miesel et al. | |
| 6,134,459 A | 10/2000 | Roberts et al. | |
| 6,198,952 B1 | 3/2001 | Miesel | |
| 6,258,046 B1 | 7/2001 | Kimball et al. | |
| 6,731,976 B2 | 5/2004 | Penn et al. | |
| 6,939,313 B2* | 9/2005 | Saadat | A61B 5/015 600/587 |
| 7,181,261 B2 | 2/2007 | Silver et al. | |
| 7,603,166 B2 | 10/2009 | Casscells, III et al. | |
| 7,618,376 B2 | 11/2009 | Kimball | |
| 7,747,301 B2 | 6/2010 | Cheng et al. | |
| 7,801,626 B2 | 9/2010 | Moser | |
| 8,000,784 B2 | 8/2011 | Ferren et al. | |
| 8,103,361 B2 | 1/2012 | Moser | |
| 8,226,578 B2 | 7/2012 | Von Malmborg | |
| 8,231,537 B2* | 7/2012 | Ahmed | A61B 5/02158 600/485 |
| 8,275,438 B2 | 9/2012 | Simpson et al. | |
| 8,298,142 B2 | 10/2012 | Simpson et al. | |
| 8,364,230 B2 | 1/2013 | Simpson et al. | |
| 8,425,416 B2 | 4/2013 | Brister et al. | |
| 8,449,464 B2 | 5/2013 | Simpson et al. | |
| 8,454,521 B2 | 6/2013 | Mochizuki | |
| 8,454,524 B2 | 6/2013 | Kassem | |
| 8,532,730 B2 | 9/2013 | Brister et al. | |
| 8,637,320 B2 | 1/2014 | Schubert et al. | |
| 8,639,309 B2 | 1/2014 | Shuler | |
| 8,744,544 B2 | 6/2014 | Najafi et al. | |
| 8,828,320 B2 | 9/2014 | Bardell et al. | |
| 8,862,197 B2 | 10/2014 | Kamath et al. | |
| 2004/0133079 A1 | 7/2004 | Mazar et al. | |
| 2006/0079923 A1* | 4/2006 | Chhabra | A61B 17/12113 606/192 |
| 2006/0253023 A1* | 11/2006 | Lewis | A61B 8/12 600/427 |
| 2007/0066929 A1 | 3/2007 | Ferren et al. | |
| 2009/0043191 A1* | 2/2009 | Castella | A61B 5/0066 600/425 |
| 2009/0105799 A1 | 4/2009 | Hekmat et al. | |
| 2009/0203064 A1 | 8/2009 | Ericson | |
| 2009/0318757 A1 | 12/2009 | Singh | |
| 2010/0036209 A1 | 2/2010 | Ferren et al. | |
| 2011/0077528 A1* | 3/2011 | Kemp | A61B 5/0066 600/476 |
| 2012/0108968 A1* | 5/2012 | Freiburger | A61B 8/0825 600/443 |
| 2014/0180069 A1 | 6/2014 | Millett | |
| 2014/0194704 A1 | 7/2014 | Millett et al. | |
| 2014/0200438 A1 | 7/2014 | Millett et al. | |

OTHER PUBLICATIONS

"Acidosis and Alkolosis." Anatomy & Physiology 5/e Student Online Learning Center. The McGraw-Hill Companies, 1998. Web. Dec. 9, 2016.*

Cell Death and Differentiation (2004), "Alterations of intracellular pH homeostasis in apoptosis: origins and roles", D. Lagadic-Gossmann, L. Huc and V. Lecureur, p. 953-961.

Seminars in Nuclear Medicine, vol. XXXIII, No. 1 (Jan. 2003), "Neuroimaging in Cerebrovascular Disorders: Measurement of Cerebral Physiology After Stroke and Assessment of Stroke Recovery", J.M. Mountz, H.G. Liu and G. Deutsch, p. 56-76.

Laboratory Animals Ltd. Laboratory Animals (2003) 37, "$CO_2$ induced acute respiratory acidosis and brain tissue intracellular pH: a $^{31}$P NMR study in swine", L. Martoft, H. Stodkilde-Jorgensen, A. Forslid, H.D. Pedersen and P.F. Jorgensen, p. 241-248.

Makaha Medical, Proof of Concept Experiment, Revision: A, Document No. MMTR 122612-01, M. Levine, Date of Experiment: Dec. 14, 2012.

Normal Breathing Defeats Chronic Diseases, "$CO_2$, Blood pH and Respiratory Alkalosis", www.NormalBreathing.com.

Interface Focus published online Mar. 23, 2011, "Modelling of pH dynamics in brain cells after stroke", P. Orlowski, M. Chappell, C.S. Park, V. Grau and S. Payne, p. 1-9.

* cited by examiner

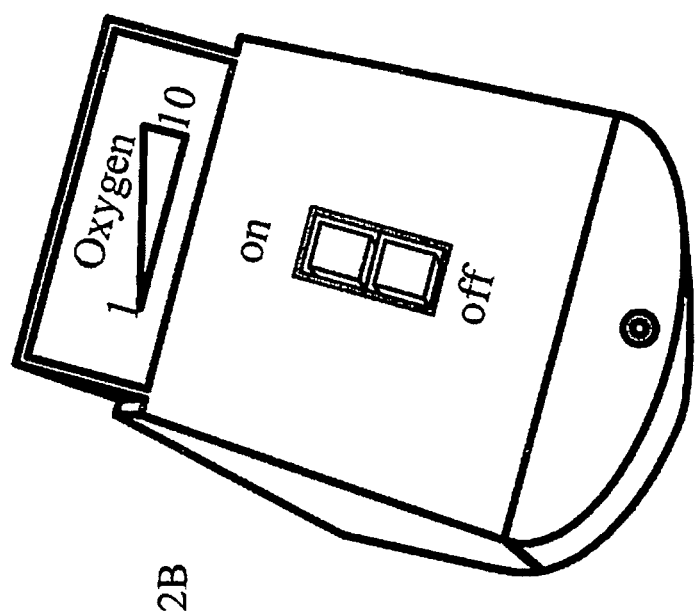

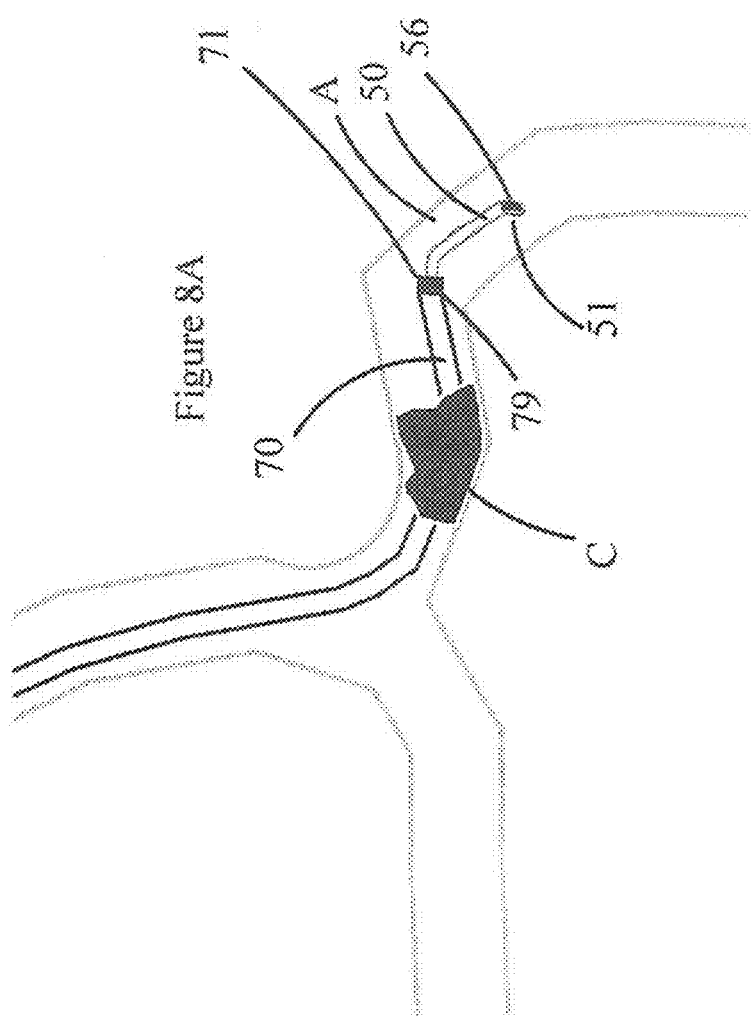

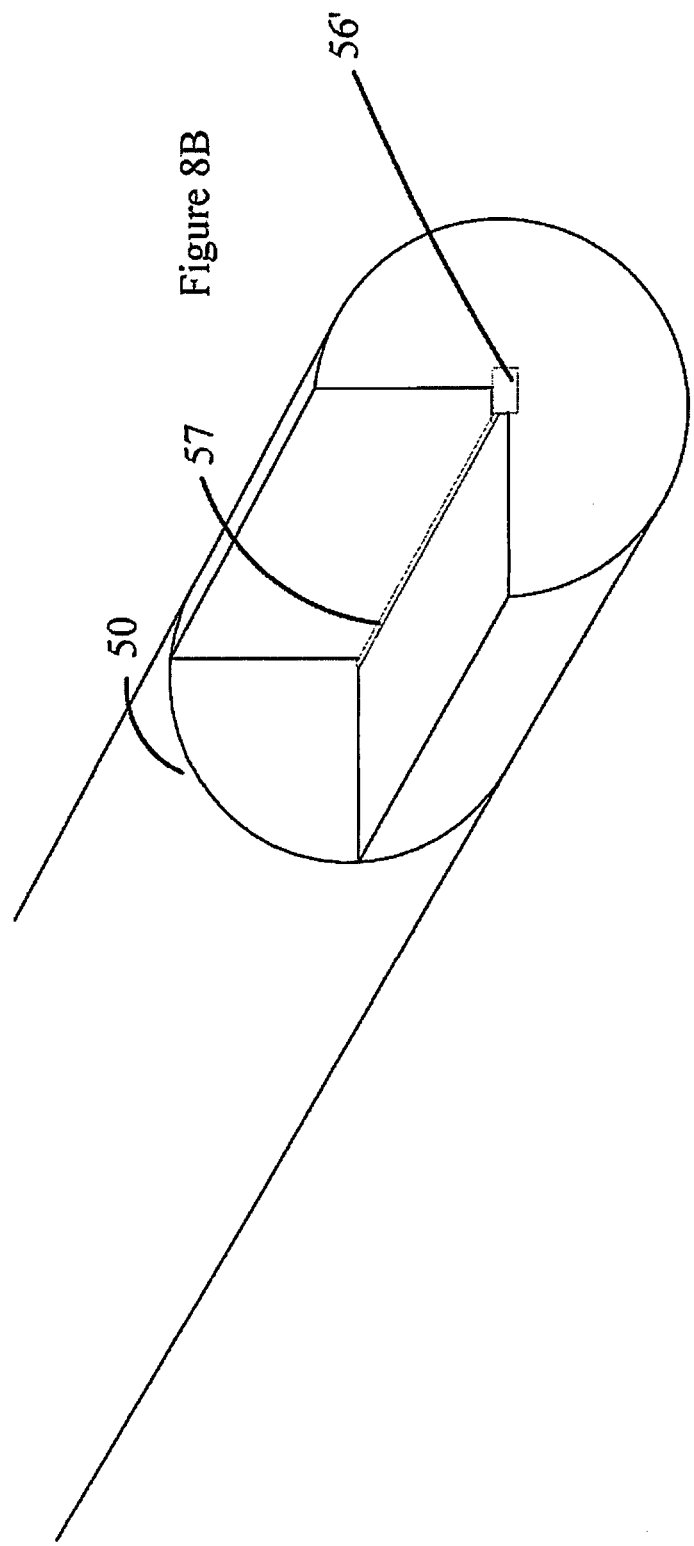

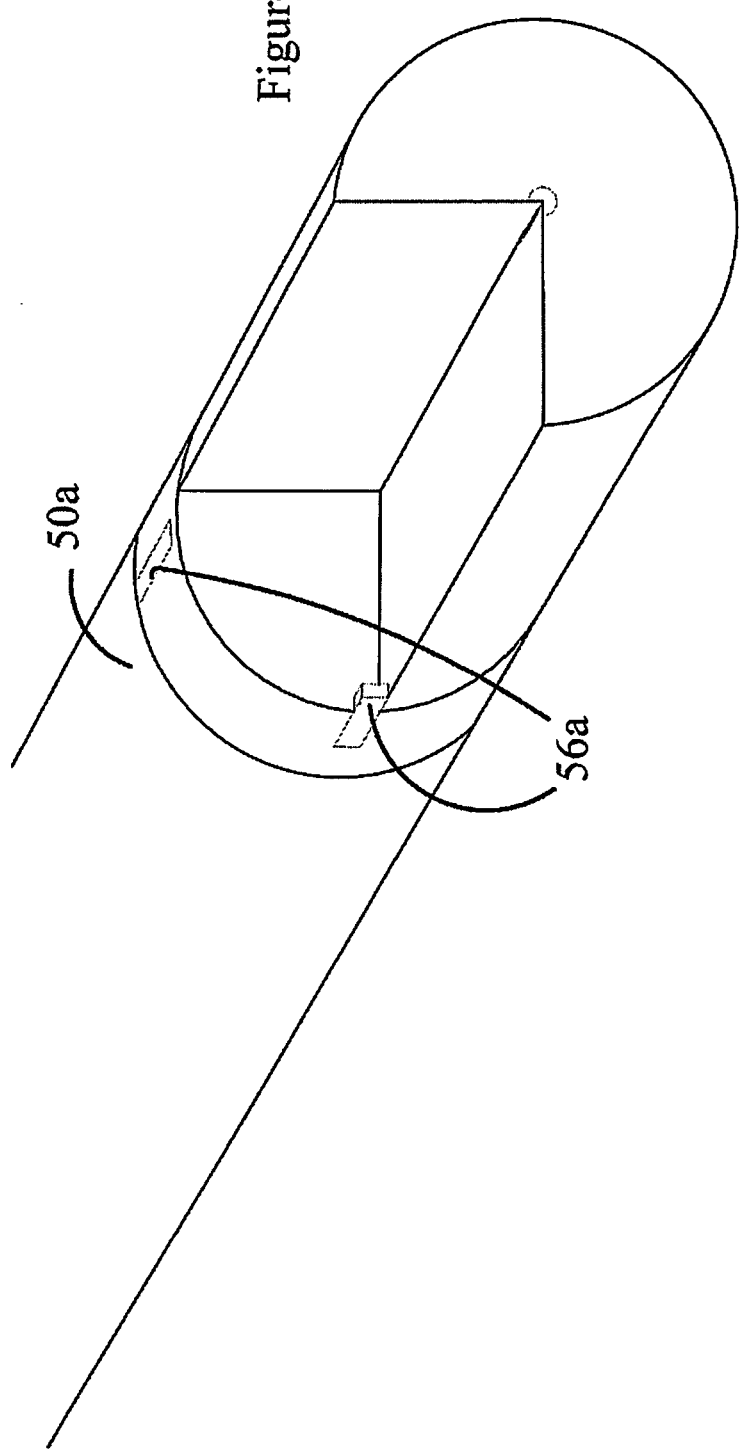

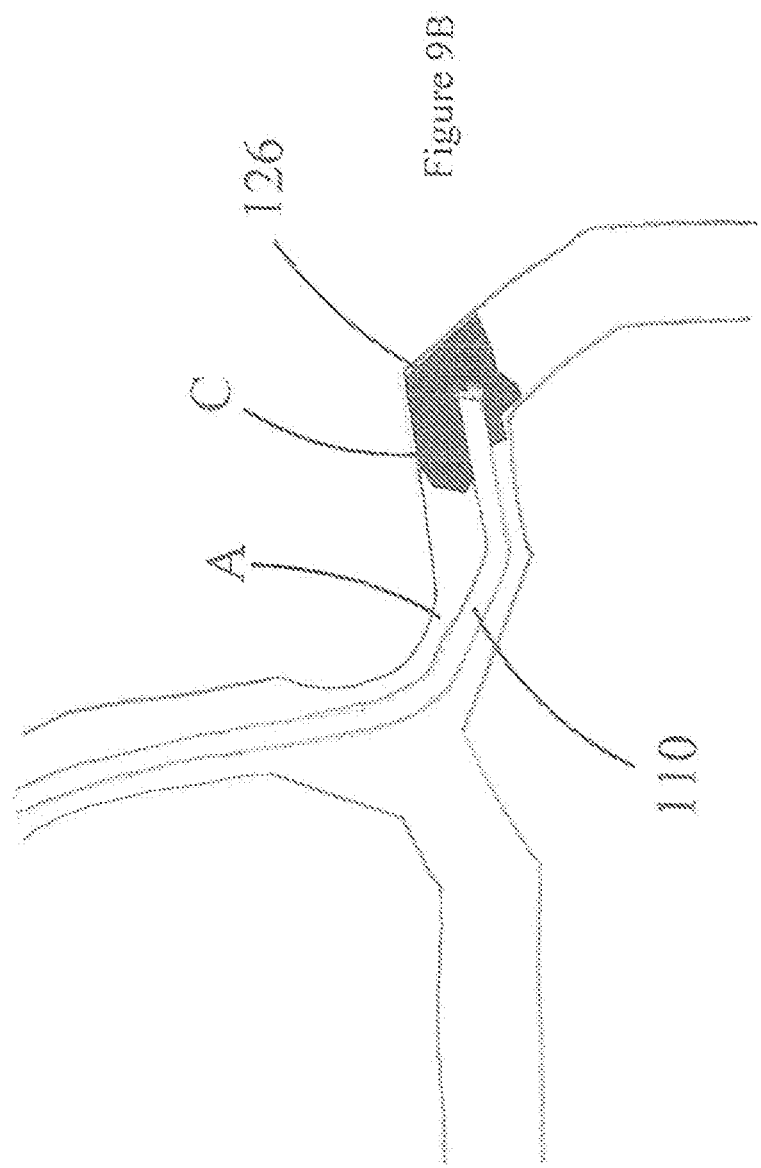

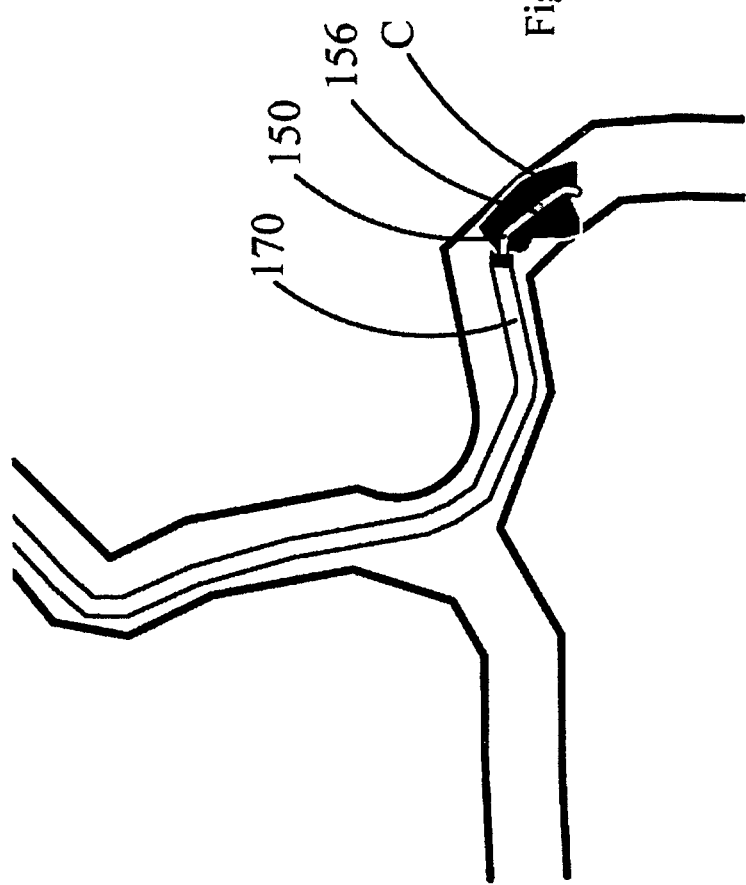

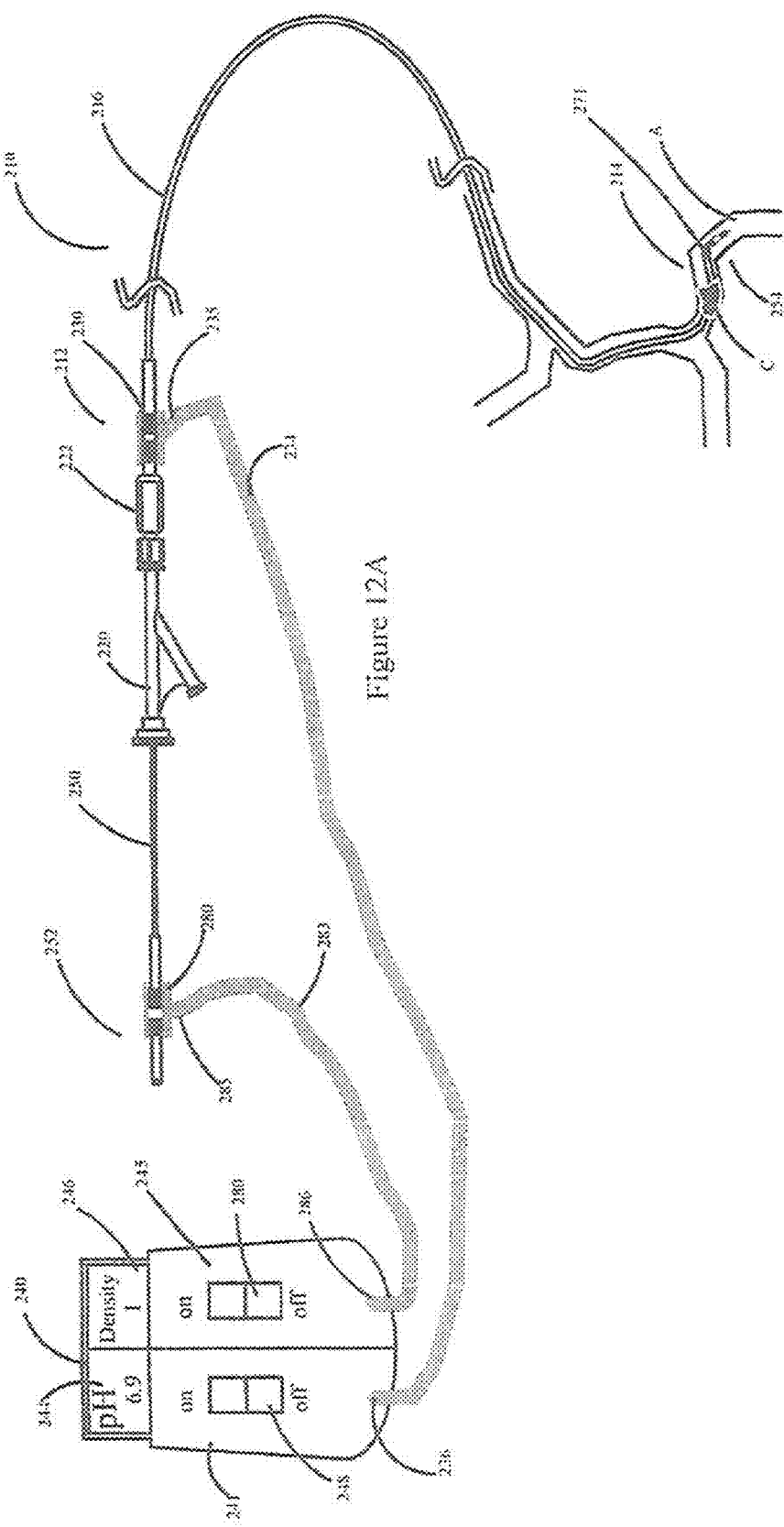

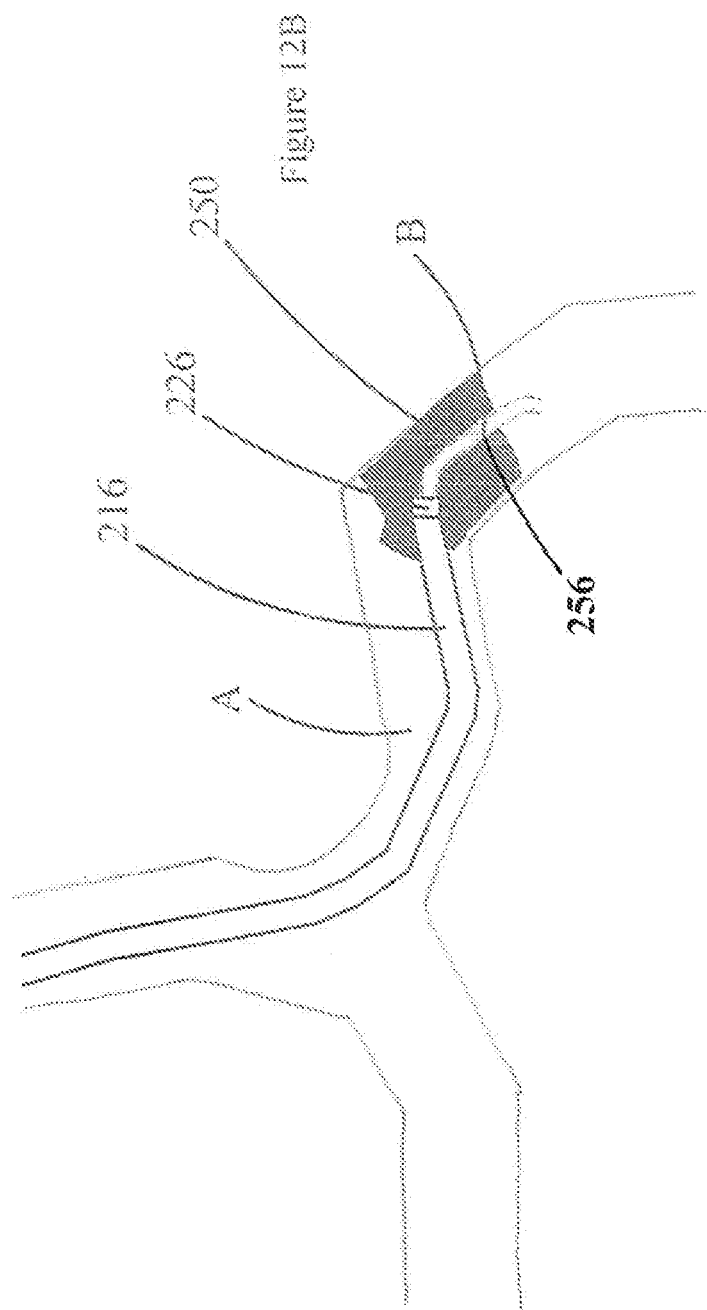

SYSTEMS AND METHODS FOR ASSESSING VASCULATURE HEALTH AND BLOOD CLOTS

This application claims priority from provisional application Ser. No. 61/718,107, filed Oct. 24, 2012, the entire contents of which are incorporated herein by reference.

BACKGROUND

Technical Field

This application relates to a system for determining the health of the vasculature to enable the surgeon to assess the advisability of blood clot removal. This application also relates to a system for identifying the composition of a blood clot in a vessel to enable the physician to scientifically determine the clot makeup to determine the best course of treatment for the clot.

Background of Related Art

Cerebrovascular disease refers to diseases of the brain caused by vascular abnormalities which result in abnormal cerebral blood flow. The most common cause of cerebrovascular disease is narrowing of the major arteries supplying blood to the brain, resulting in thrombogenic disease or sudden occlusion of blood flow, which if large enough results in ischemic stroke.

Clots (Ischemic Stroke) can originate in various areas and be caused by different modalities. These different modalities create clots that vary in consistency. The clot can be platelet rich (runny) or fibrin rich (hard) or anywhere in between the two. Ischemic stroke is caused by the thrombosis of a major vessel supplying blood to a region of the brain. A shortage of blood in the cerebral tissue leads to the deletion of metabolites such as oxygen and glucose, which in turn causes depletion of energy stores of the cells. Therefore, it is critical to remove the clots to restore adequate blood supply to the brain.

Current treatments for clot removal include mechanical thrombectomy devices and application of thrombolytic drugs to dissolve the clot. A problem encountered with these approaches is that the composition of the clot is undetectable in situ, while the efficacy of these approaches is dependent in part on the clot composition. Therefore, the physician is taking one of the known approaches for treatment of the clot without the knowledge of the clot makeup, e.g., its consistency. This can lead to inconsistent results as well as failure to properly treat the clot.

It would therefore be beneficial if the surgeon could identify the type of clot beforehand to better assess how the clot could be treated. Such prior knowledge would greatly enhance clot removal as the surgeon can adapt the approach to better match the treatment device or drugs with the type of clot.

In addition, in cerebrovascular disease, the vitality of the vasculature distal to the clot is compromised once the clot lodges in place. Vasculature that has been deprived of oxygenated blood will necrose and become friable. Once blood flow is restored after clot removal, such blood flow could potentially cause a hemorrhagic event, which means the vessel can bleed out and burst open. Currently, surgeons do not have adequate knowledge of the vasculature downstream of the clot and therefore cannot accurately assess the risk of clot removal.

It would be beneficial if the surgeon could determine the health of the vasculature distal to the clot prior to removal of the clot so the surgeon could determine if clot removal is advisable and/or take necessary precautions during clot removal so the vessels are not compromised. Prior attempts to measure pH using magnetic resonance imaging (MRI) technique have been attempted, as explained for example in "Modelling of pH Dynamics in Brain Cells After Stroke", by Piotr Orlowski, et al., published in Interface Focus, The Royal Society, 2011. However, these attempts to date have been unsuccessful. Additionally, relying on MRI is very expensive and requires relatively complex mathematical models. Therefore, although the role of pH is recognized, the need exists to utilize this parameter to readily determine vascular tissue health to enhance blood clot removal or prevent clot removal where the risk is too great.

SUMMARY OF THE INVENTION

The present invention provides a system and method for assessing vasculature downstream of the clot and a system and method for assessing the blood clot. The two systems can be used independently, or alternatively, can be used together as either separate systems or a single (combined) system.

In one aspect, the present invention provides a system for determining a pH level of blood in a vessel of a patient. The system comprises a flexible elongated member configured and dimensioned for insertion in the vessel of the patient, the elongated member having a proximal portion and a distal portion and configured for insertion so the distal portion extends past a blood clot for positioning of the distal portion distal of the blood clot. A sensor is positioned at the distal portion of the elongated member for positioning distal of the blood clot. A connector connects the elongated member to an indicator, the sensor measuring the pH level of blood, preferably in a closed or a substantially closed system downstream of the blood clot, to thereby determine pH of the vessel downstream of the blood clot to determine the condition of the vessel to assess subsequent treatment of the blood clot. The indicator provides an indication of the blood pH measured by the sensor.

In one embodiment, the flexible elongated member comprises a catheter. In another embodiment, the flexible elongated member comprises a guidewire.

In one embodiment, the sensor is embedded in a wall of the elongated member. In another embodiment, the sensor is positioned on an outer surface of the elongated member.

The system can include in some embodiments a second sensor for sensing a parameter of the blood clot and a second indicator to indicate the sensed parameter, the second sensor connected to the second indicator. In some embodiments, the second sensor senses a density of the blood clot. In some embodiments, the second sensor is positioned on a second elongated member coaxial with the elongated member carrying the sensor for measuring pH. In some embodiments, the second sensor is proximal of the first sensor.

In accordance with another aspect, the present invention provides a method for determining a pH level of blood downstream of a blood clot in a vessel of a patient comprising the steps of:

providing an elongated flexible member;

inserting the flexible member through vasculature of the patient and past the blood clot to a position downstream of the blood clot in the vessel;

sensing a pH level of the blood downstream of the clot; and indicating to the user the pH level of the blood to enable the user to determine a pH level of the vessel downstream of the blood clot for subsequent selection of a clot treatment approach.

In some embodiments, the method further comprises the step of determining a density of the blood clot to determine a clot treatment method. In some embodiments, the step of determining the density of the blood clot utilizes a sensor proximal of a sensor used for sensing pH of the blood. In some embodiments, one of the density sensor and pH sensor is on a first elongated flexible member and the other sensor is on a second elongated flexible member coaxial with the first elongated member.

In accordance with another aspect, the present invention provides a system for determining an oxygen level of blood in a vessel of a patient. The system comprises a flexible elongated member configured and dimensioned for insertion in the vessel of the patient, the elongated member having a proximal portion and a distal portion and configured for insertion so the distal portion extends past a blood clot for positioning of the distal portion distal of the blood clot. A sensor is positioned at the distal portion of the elongated member for positioning distal of the blood clot. A connector connects the elongated member to an indicator, the sensor measuring the oxygen level of blood, preferably in a closed or a substantially closed system downstream of the blood clot, to thereby determine the oxygen level of the vessel downstream of the blood clot to determine the condition of the vessel to assess subsequent treatment of the blood clot. The indicator provides an indication of the oxygen level of the blood measured by the sensor.

In accordance with another aspect, the present invention provides a method for determining an oxygen level of blood downstream of a blood clot in a vessel of a patient comprising the steps of:
  providing an elongated flexible member;
  inserting the flexible member through vasculature of the patient and past the blood clot to a position downstream of the blood clot in the vessel;
  sensing an oxygen level of the blood downstream of the clot; and
  indicating to the user the oxygen level of the blood to enable the user to determine an oxygen level of the vessel downstream of the blood clot for subsequent selection of a clot treatment approach.

In accordance with another aspect of the present invention, a system for determining a density of a blood clot in a vessel of a patient for subsequent selection of a treatment method is provided. The system comprises a flexible elongated member configured and dimensioned for insertion in the vessel of the patient, the elongated member having a proximal portion and a distal portion and the distal portion configured for insertion adjacent the blood clot. A sensor is positioned at the distal portion of the elongated member. A connector connects the elongated member to an indicator, the sensor determining the density of the blood clot and the indicator providing an indication of the determined density.

In one embodiment, the flexible elongated member comprises a catheter. In another embodiment, the flexible elongated member comprises a guidewire.

The system in some embodiments further comprises a transmitter at the distal portion of the elongated member for transmitting ultrasonic waves toward the blood clot, and the density of the blood clot is determined by ultrasonic wave feedback. The system in some embodiments can further include a pH sensor for measuring pH of blood downstream of the clot and an indicator for indicating measured pH.

The present invention provides in another aspect a method for determining a density of a blood clot in a vessel of a patient for subsequent selection of a clot treatment method. The method comprises:
  providing a flexible elongated member configured and dimensioned for insertion in the vessel of the patient, the elongated member having a proximal portion and a distal portion, the elongated member distal portion configured for insertion adjacent a blood clot;
  transmitting ultrasonic waves toward the blood clot; and
  determining the density of the blood clot based on the ultrasonic wave feedback.

In some embodiments, the method further provides a visual indication of the determined density.

In some embodiments, the method further includes positioning the elongated member so that a distal tip extends past the blood clot and a density sensor is positioned proximal of the distal tip within the blood clot.

BRIEF DESCRIPTION OF THE DRAWINGS

Preferred embodiments of the present disclosure are described herein with reference to the drawings wherein:

FIG. 2B is a close up perspective view of an oxygen level reader;

FIG. 8A is a close up view of the guidewire of FIG. 6 positioned distal of the clot and showing the pH sensor on the outer tip of the guidewire;

FIG. 8B is a cutaway view showing the pH sensor embedded in the wall of the guidewire in accordance with an alternate embodiment;

FIG. 8C is a close up view of an alternate embodiment having a density sensor spaced from the distal tip;

FIG. 9B is a close up view of the distal portion of the catheter of FIG. 9A showing the density sensor within the clot;

FIG. 11B is a close up view of the distal portion of the guidewire of FIG. 11A, with the clot broken away to show the density sensor within the clot;

FIG. 12A is a side view of another alternate system of the present invention showing a catheter coupled to a pH reader and a guidewire coupled to a density reader, and further showing the catheter tip and guidewire positioned distal of the blood clot;

FIG. 12B is a close up view of the distal end of the catheter and guidewire of FIG. 12A, showing retraction of the catheter to expose the density sensor on the guidewire.

DETAILED DESCRIPTION OF PREFERRED EMBODIMENTS

Figure 1:
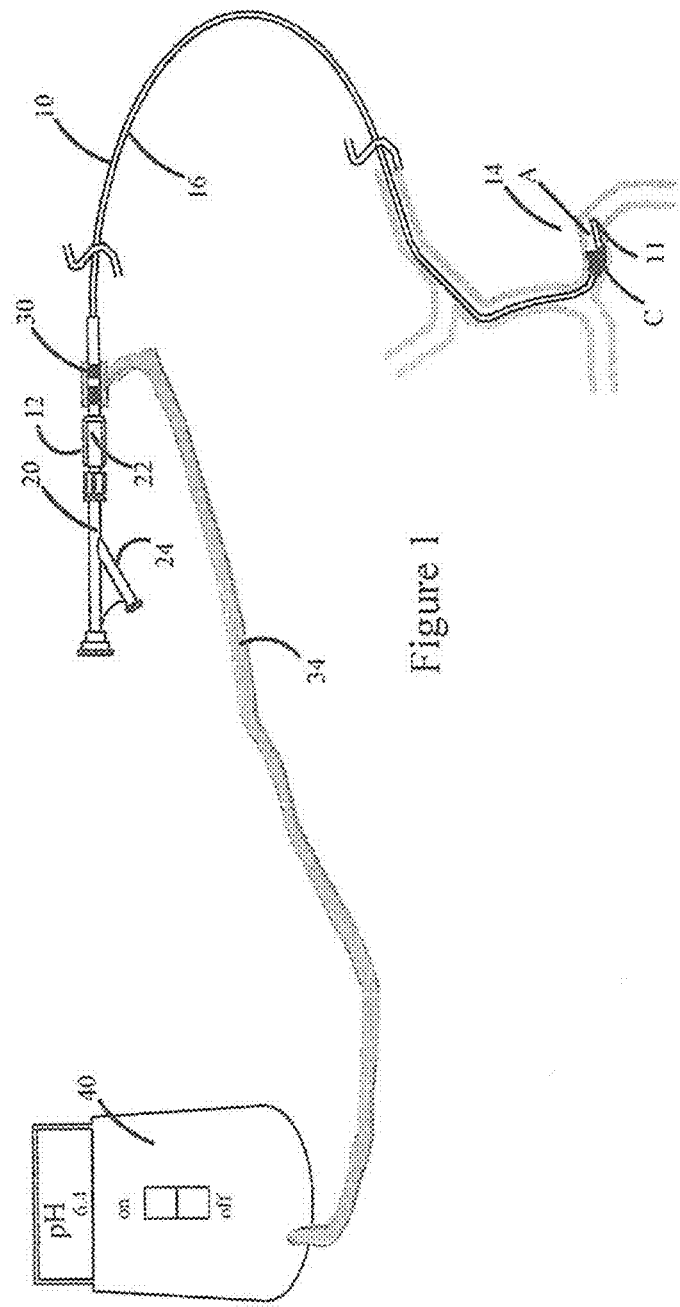
FIG. 1 is a side view of a first embodiment of the system of the present invention illustrating a catheter coupled to a pH reader and showing the catheter tip positioned distal of the blood clot.

The present invention provides a system for determining the health or condition of the vasculature distal of the blood clot. This aids the physician in assessing the effect of removal of the blood clot from the vessel. The present invention also provides a system for determining the type of blood clot. This enables the physician to assess the best mode of treatment of the blood clot. These two systems can be used independently or alternatively can be used together. That is, it is contemplated that only one of the systems is utilized so the user measures only one of the parameters, i.e., either health of vasculature or type of clot. However, it is also contemplated that both systems be utilized so the user can determine both parameters. These systems are described in detail below.

Vasculature Determination

Turning first to the system for determining the health or condition of the vasculature, this system is illustrated in FIGS. 1-8, with FIGS. 1-5 illustrating an embodiment where the pH sensor is located on a catheter and FIGS. 6-8B illustrating an embodiment where the pH sensor is located on a guidewire. It is also contemplated that a pH sensor can be positioned on the catheter and on the guidewire, and it is also contemplated that one or more pH sensors can be positioned on the catheter and one or more pH sensors can be positioned on the guidewire. Multiple sensors would enable different regions of the blood (and therefore the vasculature) to be measured. In certain embodiments utilizing multiple pH sensors, the sensors can be spaced apart sufficiently so that a pH measurement can be taken both upstream and downstream of the blood clot for comparative purposes in assessing vasculature health.

The system for measuring pH is beneficial since in certain instances, the vitality of the vasculature distal to the clot is compromised once the clot lodges in place. Vasculature that has been deprived of oxygenated blood will necrose and become friable. Once blood flow is restored after clot removal, such blood flow could potentially cause a hemorrhagic event, which means the vessel can bleed out and burst open. Therefore, this system provides a way of determining the health of the vasculature distal to the clot so the physician could determine if clot removal is advisable or take other precautions during clot removal. That is, the physician will be able to determine if the clot should be removed based upon the pH content of the vasculature distal to the clot.

Such determination can be done measuring pH. It could also be accomplished in an alternate embodiment by sensing oxygen levels in the blood which would provide an indication of the health of the vasculature. Other parameters could also be measured.

With respect to pH, it is understood that intracellular pH is important in the maintenance of normal cell function. Blood pH is regulated by a system of buffers that continuously maintain its normal range of 7.35 to 7.45. Blood pH drop below 7 or above 7.45 can cause serious problems, including death. Studies have shown that carbon dioxide plays a vital role in blood pH abnormality. Carbon dioxide serves as a buffer. As carbon dioxide becomes depleted, the pH drops and acidosis and/or apoptosis occurs.

With the presence of a blood clot, there is essentially a closed system (or substantially closed system) created in the vasculature since blood flow downstream of the clot has mostly stopped. Being a closed system, the pH of the blood can be measured and the blood pH will be indicative of the pH of the adjacent vasculature. Thus, the measurement of the blood pH as described herein provides an inexpensive, accurate and effective way to determine the pH and thus the health of the adjacent vasculature. The pH can be measured utilizing known techniques such as an ionic potential sensor that converts the activity of a specific ion dissolved in a solution into an electric potential which can be measured. Known glass and crystalline membranes can be utilized.

It is also contemplated that instead of measuring blood pH, the oxygen level of the blood can be measured downstream of the blood clot, preferably in a closed or substantially closed system, to thereby determine the health of the vasculature.

Figure 3A:
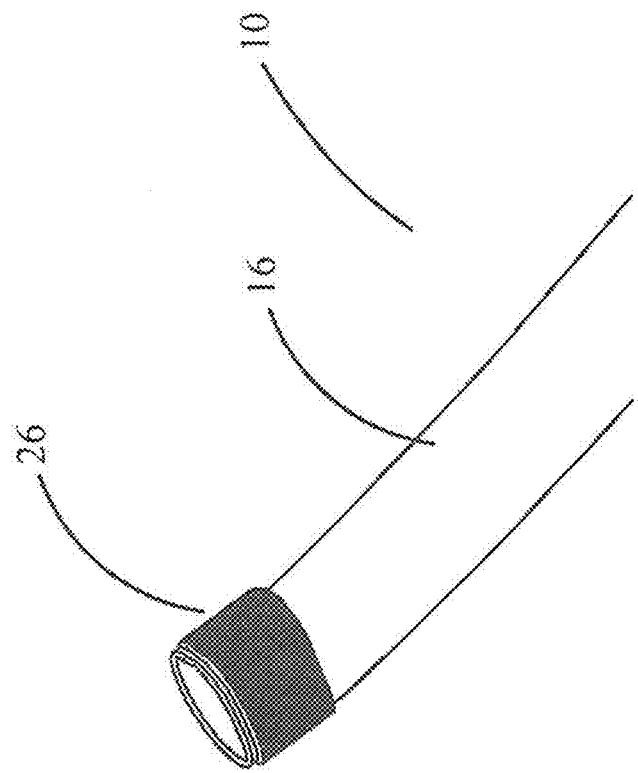
FIG. 3A is a close up view of the catheter tip of FIG. 1 showing the pH sensor on an outer surface of the catheter for determining blood pH.
Figure 3B:
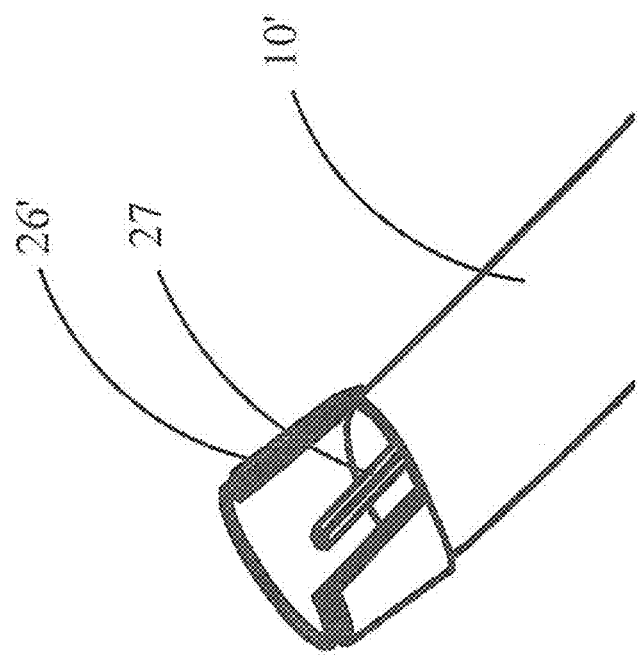
FIG. 3B is a close up view of the catheter tip showing the pH sensor embedded in the wall of the catheter in accordance with an alternate embodiment.
Figure 4:
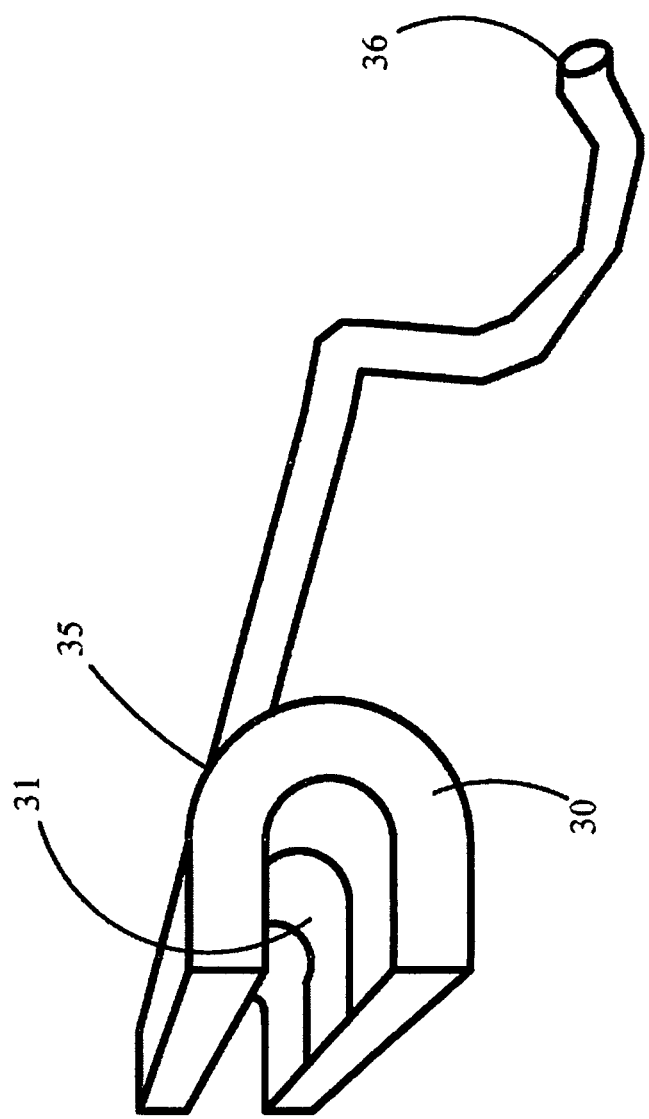
FIG. 4 is a close up perspective of the coupler of FIG. 1 for connecting the pH reader cable to the catheter.
Figure 5:
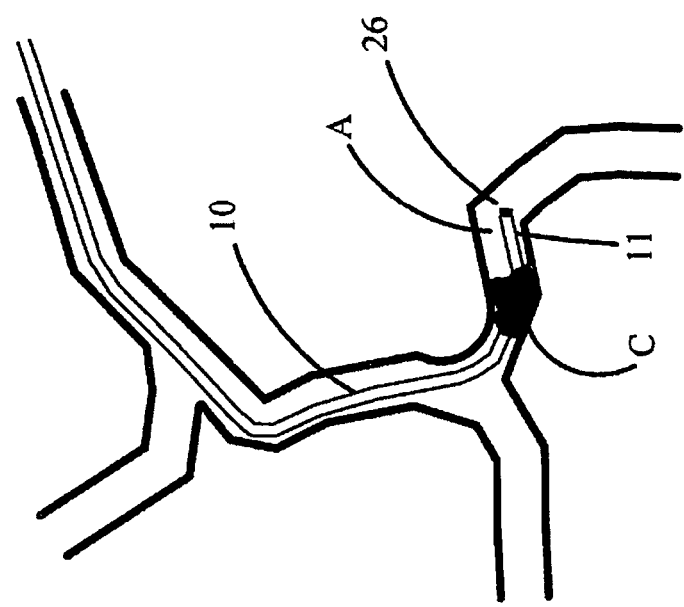
FIG. 5 is a close up view of the vasculature illustrating the catheter tip of FIG. 1 positioned past a blood clot.

Turning more specifically to the system of FIGS. 1-5, catheter 10 has a proximal portion 12 and a distal portion 14. The catheter tube 16 is sufficiently flexible to navigate the small vessels while having some rigidity to enable it to be directed around the curves of the vasculature. An RHV (rotating hemostatic valve) 20 is attached to the catheter hub 22 and includes a side arm 24 for fluid injection and/or aspiration. Coupler (connector) 30 is attached to the catheter 10, and is connected to cable 34 which is connected to pH reader (meter) 40. In one embodiment, as shown in FIG. 4, the coupler 30 is u-shaped with opening 31 between the legs of the "u" dimensioned to frictionally clamp onto the outer wall of the catheter 10. That is, the coupler 30 is shown in the embodiment of FIG. 1 in the form of a U-shaped clip with the radius of the U smaller than that of the outer wall of the catheter so it flexes outwardly when placed over the strain relief of the catheter and then is frictionally retained on the catheter. In another embodiment, a second connector (coupler) half is placed opposite the connector to form a 360 degree clip or clamp surrounding the outer wall of the catheter to retain the connector on the catheter 10. Other methods of attachment are also contemplated such as magnetic attachments. Cable 34 is connected to the coupler at one end 35 and connected at the opposing end 36 to reader 40. As shown (FIG. 1), the coupler 30 is attached to the region of catheter 10 just distal of hub 22, although other locations are also contemplated. The coupler 30 can be attached to the strain relief of the catheter 10 to enhance coupling.

The pH sensor 26 for measuring blood pH is positioned at the distal portion 14 of the catheter 10 and is electrically coupled to cable 34 via a pair of wires (not shown) extending from the sensor 26 to the coupler 30 and/or cable 34. The wires can be embedded in a wall of the catheter 10 or alternatively extend through a lumen in the catheter 10. In the embodiment of FIG. 3A the sensor 26 is positioned on an outer wall of the catheter 10, extending circumferentially around 360 degrees. The sensor can also be incorporated into a marker band at the tip of the catheter 10. In the alternate embodiment of FIG. 3B, the sensor 26' is positioned inside the catheter 10, either internal of the inner catheter wall or alternatively embedded in the wall of the catheter 10'. Wires 27 connect the sensor 26' to the conductor 30 and/or cable 24, with two lines coming into the reader 40 with two lines extending to the sensor 26.

Figure 2A:
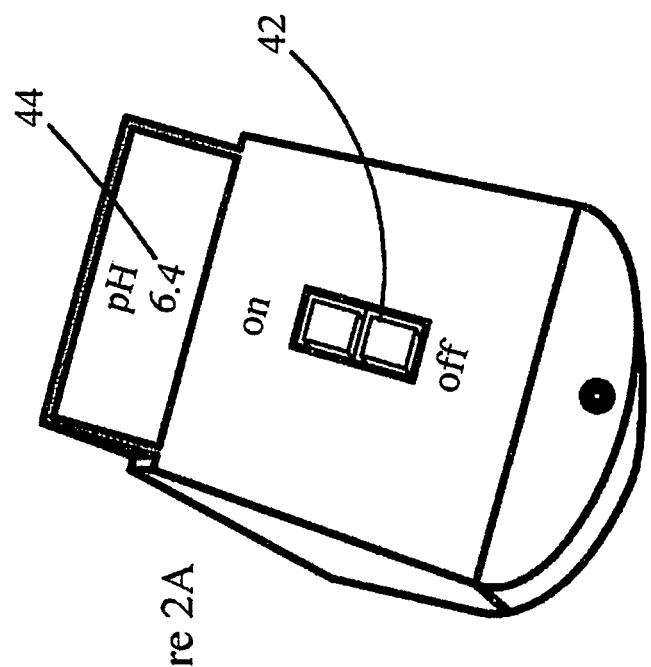
FIG. 2A is a close up perspective view of the pH reader of FIG. 1.

The pH reader 40 provides an indicator device and contains an on off switch 42. A reading 44 provides a visual indication, as a numeric value, of the measured pH of the blood to inform the user of the pH of the blood, and therefore the vasculature. FIG. 2 shows by way of example a reading of 6.4 which is below the normal range of 7.35 to 7.45 and thus indicates acidosis has likely occurred which affects (compromises) the vasculature structure.

In use, the catheter 10 (or 10') can be inserted utilizing known methods, e.g., through a femoral approach or a brachial approach, and advanced through the vascular system to the desired treatment site, e.g. a cerebral artery A. The catheter tip 11 is advanced past the blood clot C (see e.g., FIG. 5). The sensor is activated to measure pH, with the pH reader turned on so that pH value can be determined. As noted above, the closed system advantageously enables the user to determine the vasculature condition by measuring the blood pH rather than the pH of the vasculature itself. Proper treatment approaches, e.g., deciding whether the clot can be safely removed or taking other precautions to protect the vessel, can then be implemented.

Figure 6:
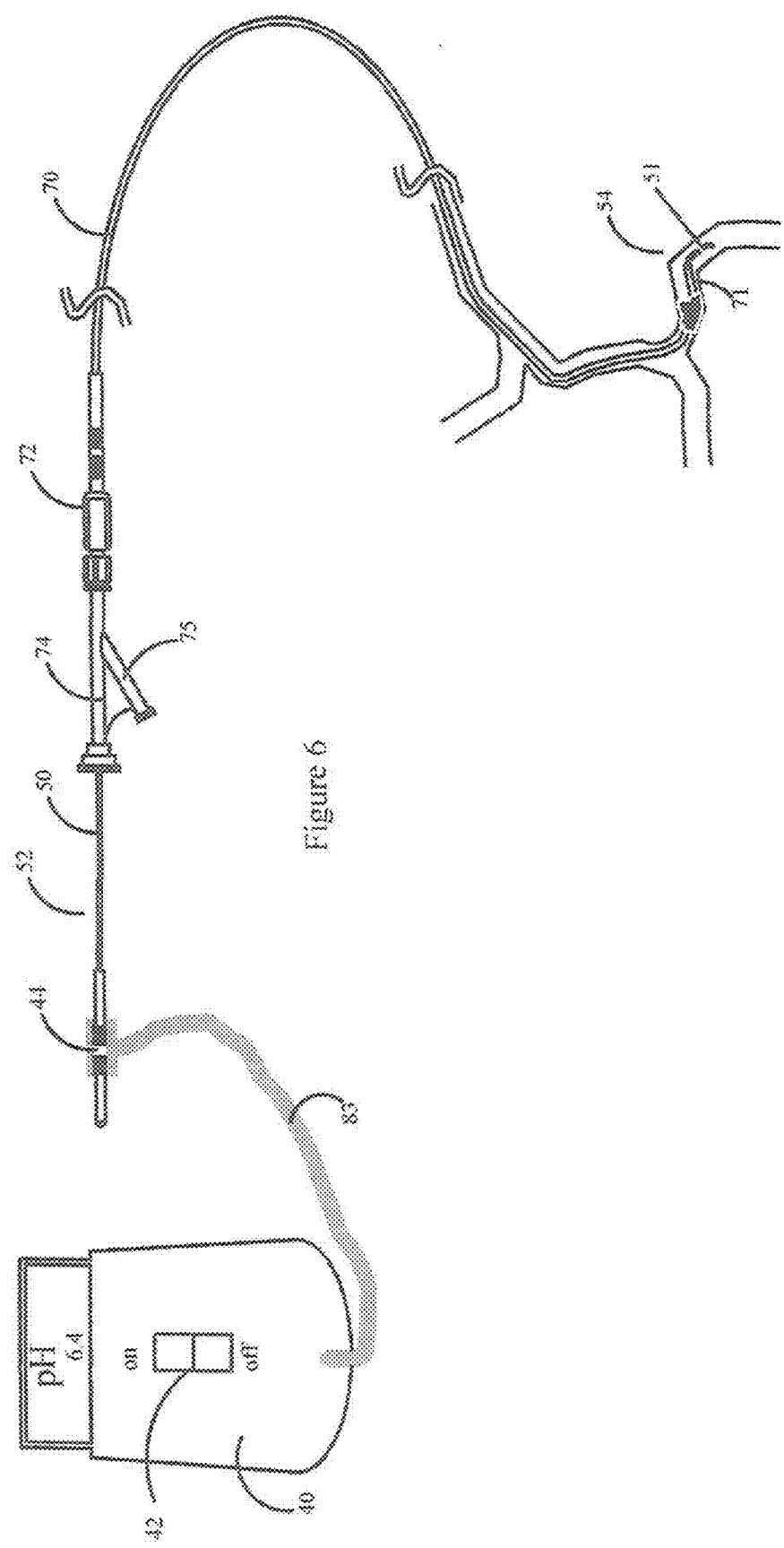
FIG. 6 is a side view of an alternate embodiment of the system of the present invention illustrating a guidewire coupled to a pH reader and showing the guidewire positioned distal of the blood clot.
Figure 7:
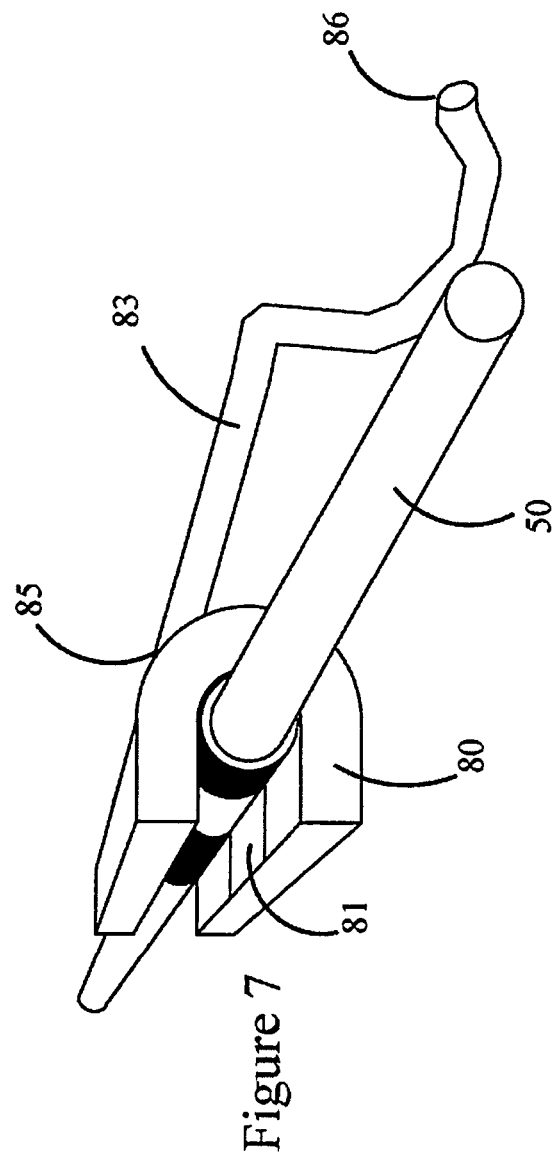
FIG. 7 is a close up perspective view of the coupler connecting the pH reader cable to the guidewire.

FIGS. 6-8B illustrate an alternate embodiment for measuring pH utilizing a sensor on a guidewire instead of the catheter as in FIG. 1. In this embodiment, guidewire 50 has a proximal portion 52 and a distal portion 54. The guidewire 50 is sufficiently rigid to navigate the small vessels while having some rigidity to enable it to be directed around the curves of the vasculature. In one embodiment the guidewire is hollow and the wire runs through the lumen from the sensor to the connector, and the wire, as in other embodiments herein, is preferably insulated. In another embodiment, the guidewire is a solid core and a polymeric jacket contains the insulated wire on an outer surface of the guidewire. The guidewire is illustrated within a lumen of a catheter 70 having a RHV 74 attached to the proximal end. The RHV 74 is attached to the hub 72 of the catheter 70 and includes a side arm 75 for injection and/or aspiration. Coupler 80 is attached to the guidewire 50, and is connected to cable 83 which is connected to pH reader 40. The pH reader can be the same as in the embodiment of FIG. 1. In one embodiment, as shown in FIG. 7, the coupler (connector) 80 is u-shaped with opening 81 between the legs of the "u" dimensioned to frictionally clamp onto the outer wall of the guidewire 50. A two part connector as described above could also be utilized. Other methods of attachment are also contemplated including magnetic attachments for example. Cable 83 is connected to the coupler 80 at one end 85 and connected at the opposing end 86 to reader 40.

The pH sensor 56 is positioned at a distal end of the guidewire 50 and is electrically coupled to coupler 80 and/or cable 84 via a pair of wires (not shown) extending from the sensor 56. The wires can be embedded in a wall of the guidewire 50 or alternatively the guidewire can have a lumen or channel through which the wires extend. In the embodiment of FIG. 8A, the sensor 56 is positioned on an outer wall of the guidewire 50, extending circumferentially around 360 degrees. The sensor can also be incorporated into a marker band at the tip of the guidewire 50. In an alternate embodiment, the sensor 56' and wires 57 (only one is shown) of guidewire 50' can be positioned inside the guidewire 50', either internal of the inner wall of the guidewire as shown in FIG. 8B, or alternatively embedded in the wall of the guidewire. The catheter 70 through which the guidewire extends can have a marker band 79. Note in FIG. 8A, the catheter 70 and guidewire 50 are positioned in a cerebral artery A distal of clot C.

In use, the switch 42 of the pH reader 40 is activated and the sensor 56 is activated to measure the blood pH and the pH reader provides a numeric pH value of the blood. FIG. 6 shows a pH reading of 6.4 by way of example. Note the guidewire 50 can be inserted utilizing known methods, e.g., through a femoral approach or a brachial approach, and advanced through the vascular system to the desired treatment site, e.g. the cerebral artery. In a preferred method, first an introducer is placed in the femoral artery, and a large guidewire and guide catheter is advanced to the carotid artery. The large guidewire is removed, and replaced with a microcatheter 70 and a smaller dimensioned guidewire 50 of the present invention which contains sensor 56. The catheter tip 71 (containing maker band 79 for imaging) and guidewire tip 51 are advanced past the blood clot C (see e.g., FIG. 8A). The sensor 56 measures the pH and transmits the measurement through the wires extending in guidewire 50 back to the cable 83 which in turn transmits it to the reader 40. As noted above, the closed system advantageously enables the user to determine the vasculature condition by measuring the blood pH rather than the pH of the vasculature (or surrounding tissue) itself. Proper treatment approaches for the treating the blood clot can then be better selected. That is, the physician can determine whether removal of the clot would be too traumatic to the vessel and risk hemorrhaging.

Note the sensors are shown at the distalmost tip of the catheter (FIGS. 1-5) or guidewire (FIGS. 6-8B) but alternatively can be spaced proximal of the distalmost tip such as the sensor 56a of guidewire 50a of FIG. 8C.

The pH sensors can be used in other applications such as in cases of gangrene or tissue dying for some other reason to intravascularly assess the vasculature or health of the tissue.

In an alternate embodiment, the oxygen level of the blood can be measured which is indicative of the oxygen and thus the health of the vasculature. The system would be the same as with the above described systems, except one or more oxygen sensors (rather than pH sensors) would be provided on the catheter or the guidewire and connected to an oxygen reader (meter) such as shown in FIG. 2B. The oxygen reader provides an indicator of the oxygen level, by providing for example a numeric value, or other indicator, to indicate a range of low to high oxygen level measurements. The sensors can be positioned on the catheter or guidewire in the similar manners of the pH sensors disclosed herein.

Clot Determination

As noted above, the present disclosure provides a system to identify a parameter such as the composition of a clot in a vessel which will enable the physician to scientifically determine the clot makeup and determine the best course of treatment from the available tool sets. This can be achieved in accordance with one embodiment using ultrasound.

More specifically, in the embodiment utilizing ultrasonic waves, the density of the clot can be estimated, in vivo, by determining the time it takes for an ultrasonic sound wave to "bounce" back from the clot. The longer the signal takes to return, the less dense the clot is. That is, an ultrasound signal will return more quickly when interacting with a denser substrate. The average densities of traditional "soft" clot or normal clot and the denser fibrin clot is determined to provide predetermined parameters, and then the system of the present disclosure compares the signal generated by the ultrasonic wave to these parameters to inform the physician of the type of clot. Thus, the system utilizes a logic circuit to determine the makeup of the clot quickly, efficiently and effectively. By way of example, a soft clot can be assigned a numeral 1 and a hard clot assigned a numeral 10, and the clot density measured to assign a value within this range so the physician would first be informed of the type of clot before taking treatment steps, such as removal of the clot. In other words, the measured average densities of both normal clot and fibrin will provide a "baseline" incorporated into the logic-circuit which will determine, in vivo during the surgical procedure, which clot type is present within the vessel. Other numeric values or indicators are also contemplated to indicate varying densities.

To generate and provide a digital or analog readout of these ultrasound signals a piezoelectric signal transducer can be used. Piezoelectric materials are crystalline structures which undergo a mechanical deformation when a certain voltage is applied to the crystal. This property is used in conjunction with an applied AC voltage applied to the crystal. As the AC voltage is applied to the piezo-material it will deform and generate a sound wave. Likewise, when a mechanical load is placed on the piezoelectric crystal a small voltage is generated. This property is used to convert an ultrasonic signal into a measurable voltage. The piezoelectric crystal has a specific voltage/frequency relationship which can be used to convert between the two.

Because of these unique properties, the same piezoelectric transducer which generates an ultrasonic signal can also be used to receive the reflected signal returning from a substrate. Utilizing these properties the ΔT (change in time) can be determined between the sent signal and the received signal by having predetermined the average ΔT for both normal and fibrin clots; the designed logic circuit will be able to determine which clot is present.

This ultrasonic signal is sent from within the vasculature to ensure that interference from cranial tissues, muscle, bone, etc. do not affect measurements. The size and shape of the piezoelectric crystal will determine the distance at which the measurement can be best made.

Figure 9A:
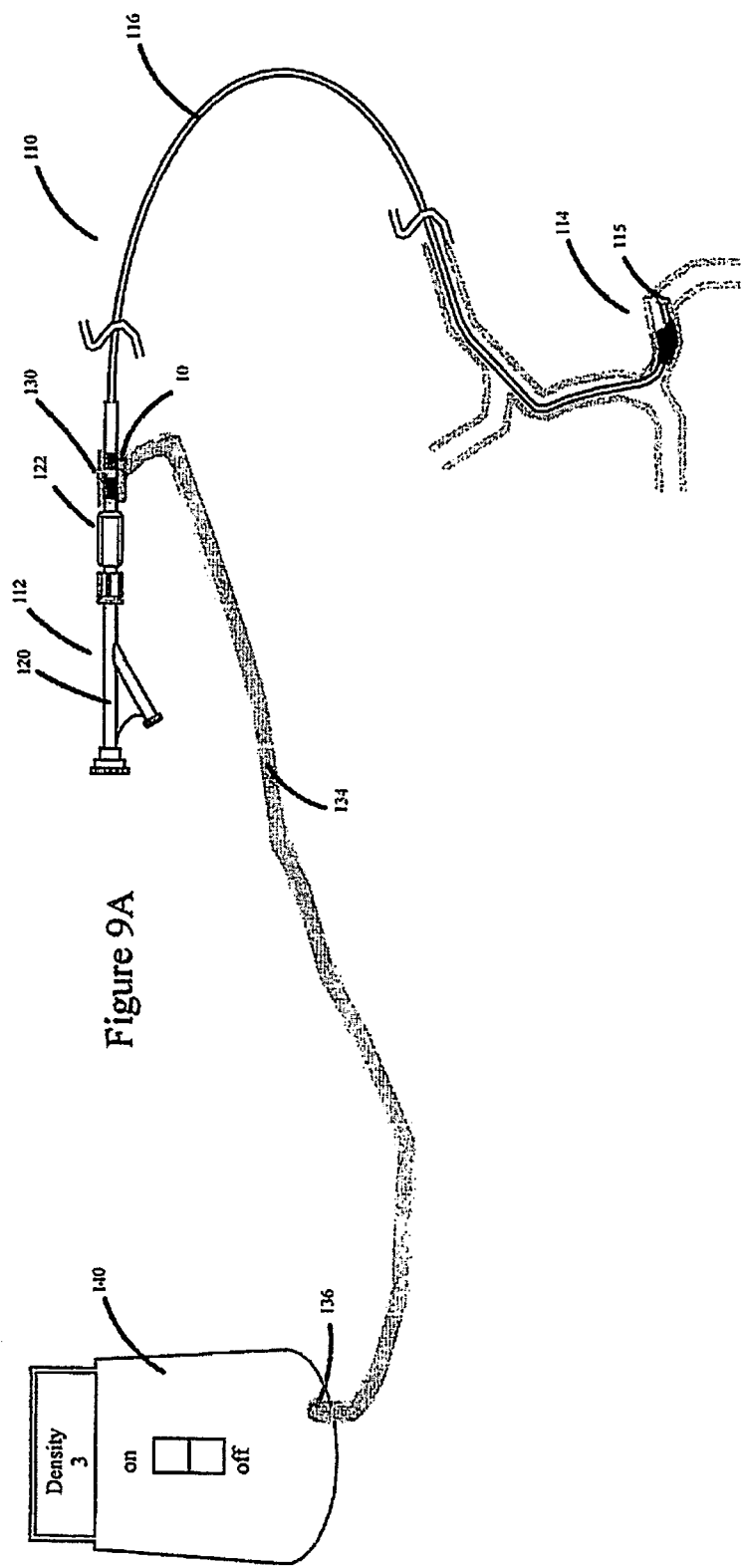
FIG. 9A is side view of an alternate system of the present invention illustrating a catheter coupled to a density reader and showing the catheter tip positioned distal of the blood clot.

Turning now to the system of FIGS. 9A-12B, a system for determining the type of clot is illustrated, with FIG. 9 illustrating an embodiment where the density sensor (utilizing ultrasound as described above) is on a catheter and FIG. 11 illustrating an embodiment where the density sensor (utilizing ultrasound) is on a guidewire. It is also contemplated that a density sensor can be positioned on the catheter and on the guidewire, and it is also contemplated that one or more density sensors can be positioned on the catheter and one or more density sensors positioned on the guidewire. This enables more than one region of the clot to be measured which could be beneficial in large clots.

Figure 10:
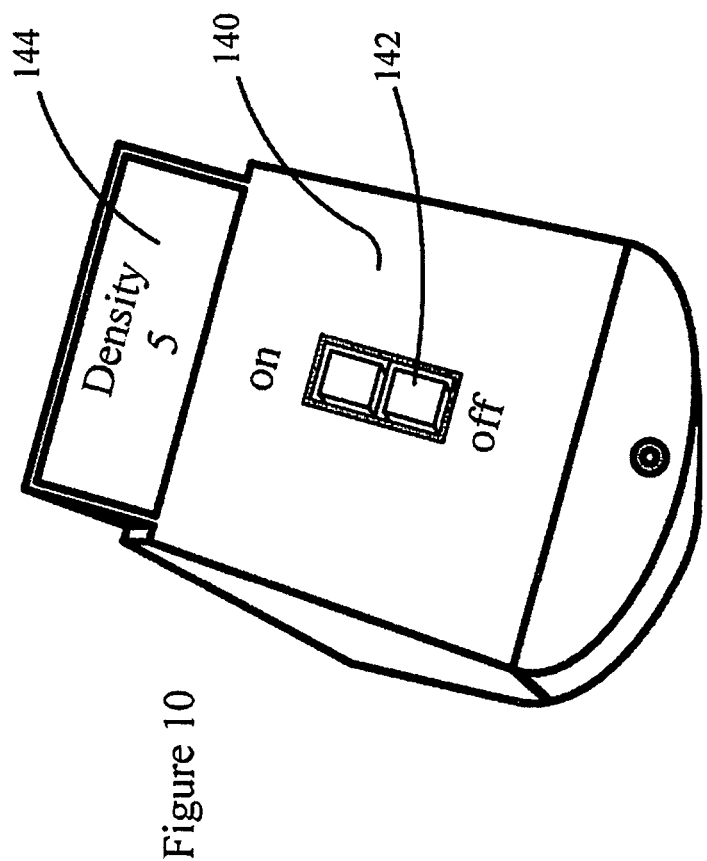
FIG. 10 is a close up view of the density reader of FIG. 9A showing a clot density reading.

Turning more specifically to the system of FIGS. 9A, 9B and 10, catheter 110 has a proximal portion 112 and a distal portion 114. The catheter tube 116 is sufficiently flexible to navigate the small vessels while having some rigidity to enable it to be directed around the curves of the vasculature. An RHV 120 is attached to the catheter hub 122 and includes a side arm 124 for fluid injection and/or aspiration. Coupler 130 is attached to the catheter 110, and is connected to cable 134 which is connected to density reader (meter) 140. In one embodiment, the coupler 130 can be the same as coupler 30 of the embodiment of FIG. 1 and can be u-shaped with an opening between the legs of the "u" dimensioned to frictionally clamp onto the outer wall of the catheter 110. That is, the coupler can be in the form of a U-shaped clip with the radius of the U smaller than that of the outer wall of the catheter so it flexes outwardly when placed over the strain relief of the catheter and then is frictionally retained on the catheter. In another embodiment, a second connector half is placed opposite the connector to form a 360 degree clip or clamp surrounding the outer wall of the catheter to retain the connector (coupler) on the catheter 110. Other methods of attachment are also contemplated such as magnetic attachments. A cable 134 is connected to the coupler at one end 135 and connected at the opposing end 136 to density reader 140. As shown, the coupler 130 is attached to the region of catheter 110 just distal of hub 122, although other locations are also contemplated.

The density sensor 126 is positioned at the distal portion 114 of the catheter 110, at the distalmost tip 115 and is electrically coupled to cable 134 via a pair of wires (not shown) extending from the sensor 126 to the coupler 130 and/or cable 134. The wires can be embedded in a wall of the catheter 110 or alternatively extend through a lumen in the catheter 110. The sensor 126 in the illustrated embodiment is at the distalmost tip but alternatively could be spaced from the distalmost end so the catheter tip can extend past the clot during use while the sensor is positioned within the clot. The sensor can be positioned on an outer wall of the catheter 110, extending circumferentially around 360 degrees. The sensor can also be positioned inside the catheter 110, either internal of the inner catheter wall or alternatively embedded in the wall of the catheter. Wires (not shown) connect the sensor to the coupler 130 and/or cable 124.

The density reader 140 provides an indicator device and contains an on off switch 142. A reading 144 provides a visual indication as a numeric value representative of a comparative density as explained above. FIG. 10 shows a density reading of "5" by way of example, indicating a clot density midway between the outer soft clot and outer hard clot range. Connector (coupler 120) is wired to the reader 140 which provides a reading of the clot type based on the signal received from the sensor 126 in response to the ultrasonic signal caused by the ultrasonic waves applied to the clot. In use, the catheter 110 can be inserted utilizing known methods, e.g., through a femoral approach or a brachial approach, and advanced through the vascular system to the desired treatment site, e.g. the cerebral artery A. The catheter tip 115 is advanced past the blood clot C (see e.g., FIG. 9B) so the sensor 126 is located within the blood clot. The sensor 126 is activated, using ultrasonic waves to measure density, with the density reader providing a visual density indication so the user can decide the optimal way to treat the clot.

Figure 11A:
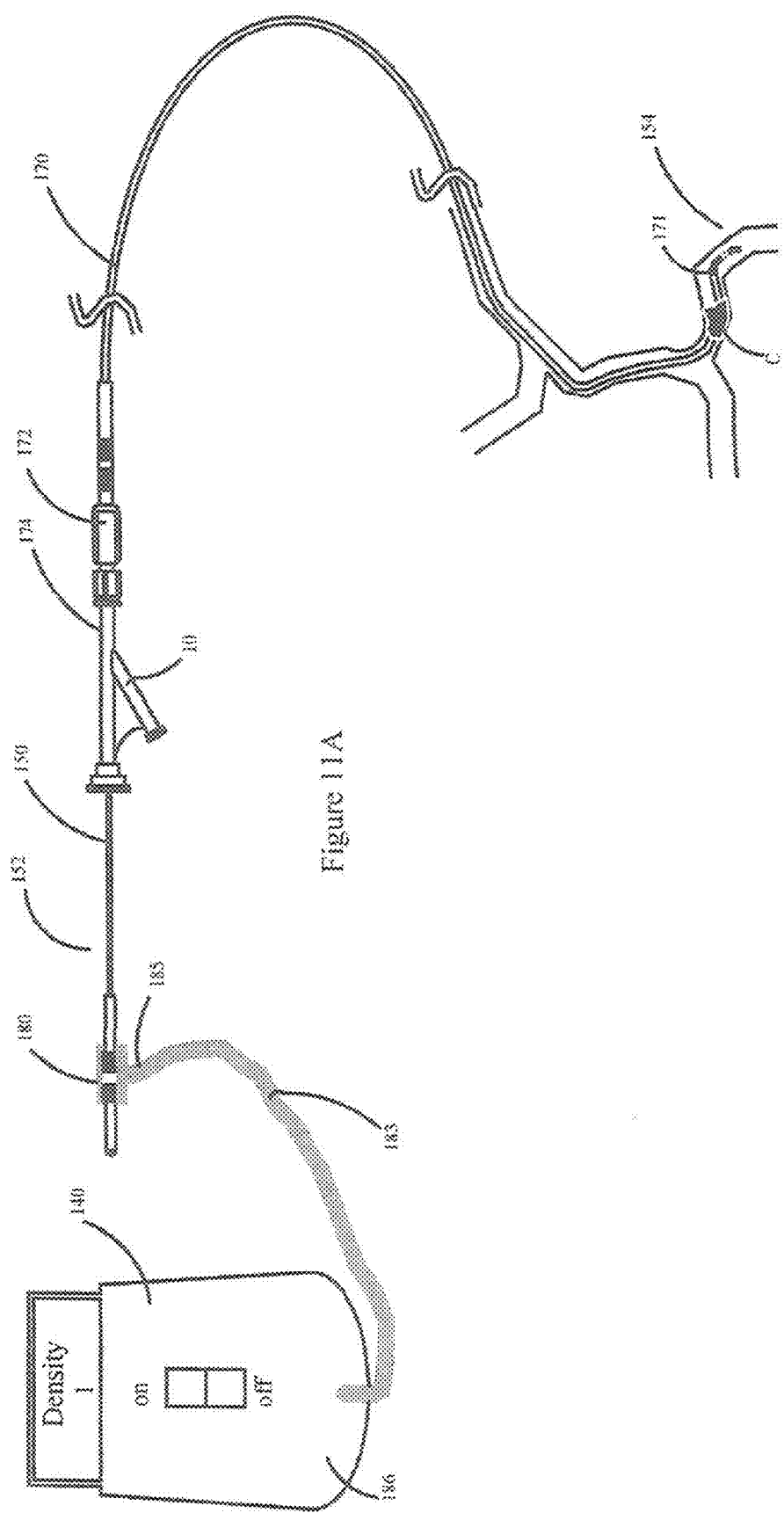
FIG. 11A is a side view of an alternate embodiment of the system of the present invention illustrating a guidewire coupled to a density reader and showing the guidewire positioned distal of the blood clot.

FIG. 11A illustrates an alternate embodiment for measuring density utilizing a sensor on a guidewire instead of the catheter as in FIG. 9A. In this embodiment, guidewire 150 has a proximal portion 152 and a distal portion 154. The guidewire 150 is sufficiently rigid to navigate the small vessels while having some rigidity to enable it to be directed around the curves of the vasculature. In one embodiment, the guidewire is hollow and the wires run through the lumen from the sensor to the connector, and the wires are preferably insulated. In another embodiment, the guidewire is a solid core and a polymeric jacket contains the insulated wires on an outer surface of the guidewire. The guidewire is illustrated within a lumen of a catheter 170 having a RHV 174 attached to the proximal end. The RHV 174 is attached to the hub 172 of catheter 170 and includes a side arm 175 for injection and/or aspiration. Coupler 180 is attached to the guidewire 150, and is connected to cable 183 which is connected to density reader 140. The density reader 140 can be the same as in the embodiment of FIG. 10. In one embodiment, the coupler is the same as coupler 80 of FIG. 7 and is u-shaped with an opening in the "u" dimensioned to frictionally clamp onto the wall of the guidewire 150. A two part connector (coupler) as described above can also be utilized. Other methods of attachment are also contemplated such as magnetic attachments. Cable 183 is connected to the coupler 180 at one end 185 and connected at the opposing end 186 to meter 140.

Density sensor 156 is positioned at a distal end of the guidewire 150, either at the distalmost tip or spaced from the distalmost tip as shown in FIG. 11B, and is electrically coupled to coupler 180 and/or cable 184 via a pair of wires (not shown) extending from the sensor 156. The wires can be embedded in a wall of the guidewire 150 or alternatively the guidewire can have a lumen or channel through which the wires extend. In the embodiment of FIGS. 11A and 11B the sensor 156 is positioned on an outer wall of the guidewire 150, extending circumferentially around 360 degrees. The sensor can also be incorporated into a marker band at the tip of the guidewire 150. In an alternate embodiment, the sensor can be positioned inside the guidewire 150, either internal of the inner wall of the guidewire in the same manner as in the embodiment of FIG. 8B, or alternatively embedded in the wall of the guidewire. The catheter 170 through which the guidewire extends can have a marker band. Note in FIG. 11A, the guidewire 150 is positioned with the sensor in the clot C and the catheter 170 is positioned in a cerebral artery A proximal of clot C.

In use, the density sensor 156 is activated to selectively measure the density of the blood clot and with switch 42 turned on, density indication is provided. Note the guidewire 150 can be inserted utilizing known methods, e.g., through a femoral approach or a brachial approach, and advanced through the vascular system to the desired treatment site, e.g. the cerebral artery. In a preferred method, first an introducer is placed in the femoral artery, and a large guidewire and guide catheter are advanced to the carotid artery. The large guidewire is removed, and replaced with a microcatheter 170 and a smaller dimensioned guidewire 150 of the present invention which contains sensor 156. The catheter tip 171 is advanced past the blood clot C. The guidewire 150 is positioned in the clot and in some embodiments the catheter 170 is withdrawn proximally to expose the sensor 156 within the clot C to measure the density of the clot and transmit the measurement through the wires extending in guidewire 150 back to the cable 183 which in turn transmits it to the reader 140. Proper treatment approaches for the treating the blood clot can then be better be selected. That is, the reader 140 is used to indicate density measurement so the physician can determine the optimal way to treat the clot.

Combination of Systems

Figure 13:
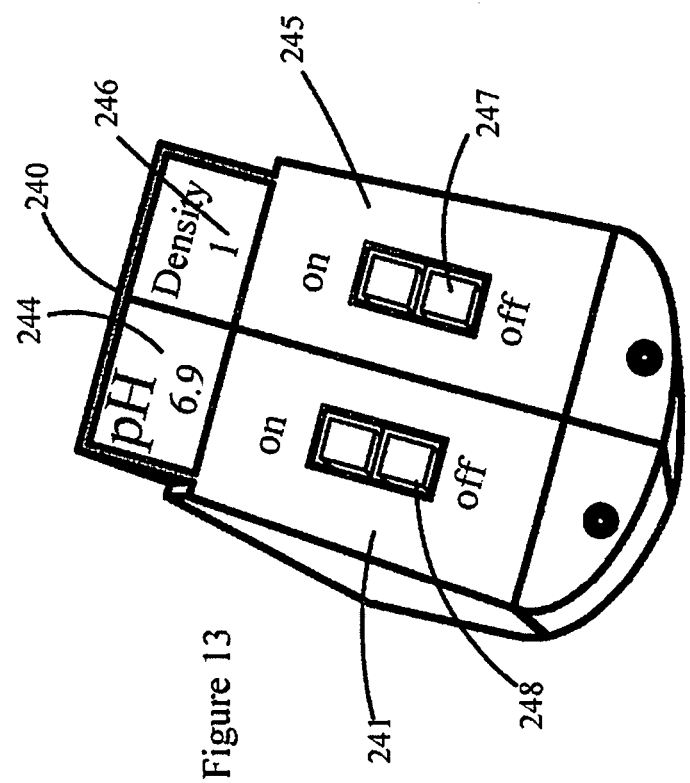
FIG. 13 is an enlarged view of the density reader of FIG. 12A.

It is contemplated that the system for determining clot density (or other clot parameter) and the system for measuring the blood pH (or other blood parameter such as oxygen) can be used together. In such system, both the density sensor and pH sensor (or oxygen sensor) along with a density and pH (or oxygen) reader are provided. Such system is shown in the embodiment of FIGS. 12A-13.

Catheter 210 has a proximal portion 212 and a distal portion 214. The catheter tube 216 is sufficiently flexible to navigate the small vessels while having some rigidity to enable it to be directed around the curves of the vasculature. An RHV 220 is attached to the catheter hub 222 and includes a side arm 224 for fluid injection and/or aspiration. Coupler 230 is attached to the catheter 210, and is connected to cable 234 which is connected to pH reader (meter) 241 of reader 240. Reader 240 provides both a pH reading and a density reading. Although shown as a single reader (meter), it is also contemplated that separate meters, such as in FIGS. 2 and 10 could be provided. In one embodiment, the coupler 230 is identical to the embodiment of FIG. 4, being U-shaped with an opening in the "u" dimensioned to frictionally clamp onto the outer wall of the catheter 210. Alternatively, a second connector (coupler) half as described above can be utilized. Other methods of attachment are also contemplated. Cable 234 is connected to the coupler 230 at one end 235 and connected at the opposing end 236 to reader 241. As shown, the coupler 230 is attached to the region of catheter 210 just distal of hub 222, although other locations are also contemplated.

The pH sensor 226, identical to the sensor of FIG. 1, is positioned at the distal portion 214 of the catheter 210 and is electrically coupled to cable 234 via a pair of wires (not shown) extending from the sensor 226 to the coupler 230 and/or cable 234. The wires can be embedded in a wall of the catheter 210 or alternatively extend through a lumen in the catheter 210. In the embodiment of FIG. 12A, the sensor is positioned on an outer wall of the catheter 210, extending circumferentially around 360 degrees in an identical manner as shown in FIG. 3A. The sensor can also be incorporated into a marker band at the tip of the catheter 210. In the alternate embodiment, the sensor can be is positioned inside the catheter 210 (similar to sensor 26' of FIG. 3B), either internal of the inner catheter wall or alternatively embedded in the wall of the catheter. The pH sensor can be positioned at the distalmost tip as shown or alternatively spaced proximally of the distalmost tip. Wires connect the sensor 236 to the coupler 230 and/or cable 224.

The pH reader 241 contains an on off switch 248 to selectively provide a readout of the measured pH. A reading 244 provides a visual indication, as a numeric value, of the measured pH of the blood for the user to determine the pH of the vasculature.

Guidewire 250 has a proximal portion 252 and a distal portion 254. The guidewire 250 is sufficiently rigid to navigate the small vessels while having some rigidity to enable it to be directed around the curves of the vasculature. The guidewire 250 is illustrated within a lumen of catheter 210. Coupler 280 is attached to the guidewire 250, and is connected to cable 283 which is connected to density reader 245 of reader 240. In one embodiment, the coupler 280 is the same as coupler 80 of FIG. 7 and is u-shaped with opening in the "u" dimensioned to frictionally clamp onto the wall of the guidewire 250. Alternatively, a second connector (coupler) half as described above can be utilized. Other methods of attachment are also contemplated. Cable 283 is connected to the coupler 280 at one end 285 and connected at the opposing end 286 to reader (meter) 245.

A density sensor 256, which is identical to sensor 156 of FIG. 11B, is positioned at a distal portion of the guidewire 250, spaced proximally of the distalmost tip, and is electrically coupled to coupler 280 and/or cable 283 via a pair of wires (not shown) extending from the sensor. The wires can be embedded in a wall of the guidewire 250 or alternatively the guidewire can have a lumen or channel through which the wires extend. In the embodiment of FIG. 12A, the sensor 256 is positioned on an outer wall of the guidewire 250 in the same manner as sensor 156 of FIG. 11B, extending circumferentially around 360 degrees. The sensor 256 can also be incorporated into a marker band at the tip of the guidewire 250. In an alternate embodiment, the sensor can be positioned inside the guidewire 250, either internal of the inner wall of the guidewire in the same manner as shown in FIG. 8B, or alternatively embedded in the wall of the guidewire. The catheter 210 through which the guidewire 250 extends can have a marker band. Note in FIG. 12A, the catheter 210 and guidewire 250 are positioned in a cerebral artery A distal of clot C. In use, the catheter 210 can be withdrawn with respect to the guidewire 250 to expose the density sensor 256 within the clot as shown in FIG. 12B where the density sensor 256 is proximal of the distal tip. In the embodiment wherein the density sensor 256 is at the distalmost tip, the guidewire 250 would be withdrawn further proximally until the distalmost tip (and sensor) is positioned in the clot.

In the embodiment where the pH sensor is on the guidewire (as in the embodiment of FIG. 6) and the density sensor is on the catheter (as in the embodiment of FIG. 9A), the catheter need not be withdrawn. The density sensor 256 can be positioned proximal of the pH sensor 226 during use since the density sensor is exposed on the outside of the catheter to measure the blood clot parameter and the pH sensor is exposed on the guidewire to measure the blood parameter downstream of the blood clot. In use, the density sensor is activated to measure clot density and switch 247 of the density reader 245 of reader 240 is turned on to provide a visual numeric indication of a relative density. The pH sensor is activated either simultaneously, or at a different time, so pH reader 241 provides a visual numeric indication of blood pH.

It is also contemplated that in some embodiments a pH sensor (or oxygen sensor) and a density sensor can both be positioned on a single guidewire or a single catheter.

Note the guidewire 250 can be inserted utilizing known methods, e.g., through a femoral approach or a brachial approach, and advanced through the vascular system to the desired treatment site, e.g., the cerebral artery. In one method, first an introducer would be placed in the femoral artery, and a large guidewire and guide catheter would be advanced to the carotid artery. The large guidewire is removed, and replaced with a microcatheter 210 which contains a pH (or oxygen) sensor (or alternatively a density sensor), and a smaller dimensioned guidewire 250 of the present invention which contains sensor 256. The catheter tip 271 is advanced past the blood clot C. The sensor 256 of guidewire 250 is positioned in the clot so the sensor measures the density of the clot and transmits the measurement through the wires extending in guidewire 250 back to the cable 283 which in turn transmits it to the density reader 245 of reader 240. (In the embodiment where the catheter contains the density sensor, the guidewire can contain the pH (or oxygen) sensor). The pH sensor 226 is positioned distal (downstream) of the blood clot to measure pH of the blood distal of the clot and transmit it via wires to the cable and pH reader 241. As noted above, the closed (or substantially closed) system advantageously enables the user to determine the vasculature condition by measuring the blood pH rather than the pH of the vasculature (and surrounding tissue) itself. Proper treatment approaches for the treating the blood clot can be better selected. The density reading provides information on the blood clot itself. As noted above, an oxygen sensor can be used in the closed or substantially closed system to determine the vasculature condition.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed:

1. A method of preventing hemorrhaging of a vessel containing a blood clot in a patient by determining in a closed system a vitality of a portion of the vessel downstream of the blood clot to determine how to treat the blood clot by determining a pH level of blood downstream of the blood clot, the method comprising the steps of:
providing an elongated flexible member having a distal portion;
inserting the flexible member through vasculature of the patient and past the blood clot to a select position downstream of the blood clot in the vessel so the distal portion is positioned distal of the blood clot, the flexible member carrying a pH sensor;
after the pH sensor is in position distal of the blood clot, sensing the pH level of the blood downstream of the blood clot with the sensor positioned distal of the blood clot, the pH level of the blood downstream of the blood clot in the closed system indicative of the vitality of the vessel downstream of the blood clot; and
visually displaying to the user, via an indicating device in communication with the sensor, the pH level of the blood downstream of the blood clot prior to commencement of treatment of the blood clot to assess the vitality of the portion of the vessel downstream of the blood clot; and
subsequently determining to keep permanently in place the flood clot based on the pH level in the preceding displaying step falling outside a predetermined normal range to thereby prevent subsequent hemorrhaging of the vessel.

2. The method of claim 1, further comprising the step of determining a density of the blood clot to determine a clot treatment method.

3. The method of claim 1, wherein the step of determining the density of the blood clot utilizes a density sensor for transmitting ultrasonic waves.

4. The method of claim 3, wherein one of the density sensor and pH sensor is carried by a first elongated flexible member and the other sensor is carried by a second elongated flexible member coaxial with the first elongated member.

5. The method of claim 1, wherein the sensor remains distal of the blood clot during the entire sensing function.

6. The method of claim 1, wherein the step of keeping the blood clot occurs if the pH level falls below a predetermined range to indicate occurrence of acidosis compromising the vasculature.

7. The method of claim 1, wherein the predetermined normal range is a range of 7.35 to 7.45.

8. The method of claim 1, wherein the vitality of the vessel is assessed to treat cerebrovascular disease.

9. The method of clam 1, further comprising the step of taking a measurement of the blood pH upstream of the clot utilizing a second pH sensor carried by the flexible member and positioned proximal of the pH sensor positioned distal of the clot for comparative assessment.

10. The method of claim 1, wherein the flexible elongated member and the pH sensor are inserted through a femoral approach.

11. The method of claim 1, wherein the flexible elongated member and the pH sensor are inserted through a brachial approach.

* * * * *